United States Patent [19]

Dubocovich

[11] Patent Number: 5,093,352

[45] Date of Patent: Mar. 3, 1992

[54] ANTIDEPRESSANT AGENTS

[75] Inventor: Margarita L. Dubocovich, Evanston, Ill.

[73] Assignee: Whitby Research, Inc., Richmond, Va.

[21] Appl. No.: 524,584

[22] Filed: May 16, 1990

Related U.S. Application Data

[63] Continuation-in-part of Ser. No. 274,631, Nov. 14, 1988, abandoned, which is a continuation of Ser. No. 86,377, Aug. 17, 1987, abandoned.

[51] Int. Cl.$^5$ .............................................. A61K 31/40
[52] U.S. Cl. ..................................................... 514/419
[58] Field of Search ................................ 514/419, 420

Primary Examiner—Stanley J. Friedman
Attorney, Agent, or Firm—Walter A. Hackler; Richard J. Hammond

[57] ABSTRACT 2-aryl substituted N-acetyl tryptamines are utilized as antidepressant agents.

18 Claims, 3 Drawing Sheets

ANTIDEPRESSANT AGENTS

This application is a continuation-in-part of U.S. Serial No. 274,631, filed Nov. 14, 1988, now abandoned, which was a continuation of U.S. Ser. No. 086,377, filed Aug. 17, 1987, now abandoned.

BACKGROUND OF THE INVENTION

1. Field of the Invention

This invention relates to a new method of use of 2-aryl substituted N-acetyl tryptamines as antidepressant agents.

2. Background of the Art

Melatonin, 5-methoxy-N-acetyl tryptamine is produced in the pineal gland. The synthesis and secretion of melatonin exhibit a circadian rhythm that changes with the seasons and with age, e.g., pubescence and senescence. The rhythm appears to be the result of both endogenous mechanisms and environmental cues, most notably the exposure of mammals to light, which inhibits melatonin synthesis and secretion. Melatonin is thought to be the hormonal mediator of photoperiodic changes. Evidence suggests that melatonin is involved in the regulation of circadian rhythms and a variety of neural and endocrine functions.

Numerous neuroendocrine functions have been attributed to the hormone melatonin with a main site of action at the level of the hypothalamic-pituitary axis. [See Minneman and Wurtman, *Life Science*, 17:1189-1200 (1975), and Cardinali, et al., *Endocrinoloov*, 105:437-441 (b 1979)]. However, the lack of suitable in vitro preparation has hindered the characterization of the melatonin receptor and the screening of potential melatonin receptor antagonist. In the past, melatonin responses have been studied on amphibian dermal melanocytes, using in vivo [Quay and Bagnara, *Arch. Int. Pharmacodyn. Ther.*, 150:137-143 (1964)], or in vitro methods [Heward and Hadley, *Life Sci.*, 17:1167-1168 (1975). Melatonin at picomolar concentrations has been found to inhibit the calcium-dependent release of $H^3$ dopamine from the rabbit retina in vitro [Dubocovich, *Nature* 306:782-784 (1983)]. This assay appears to be more sensitive and a better quantitative technique to determine the potency of melatonin and related compounds than the photometric measurement of reflectance in amphibian dermal melanocytes after exposure to these compounds (Quay and Bagnara, supra). Dubocovich [*Journal of Pharmacology and Experimental Therapeutics*, 234:395-401 (1985)] describes the structure-activity relationship of melatonin and related indoles on the calcium-dependent release of $^3H$ dopamine and the properties of N-acetyl tryptamine (Heward and Hadley, supra) as a melatonin receptor antagonist using the rabbit or chicken retina. By the use of this assay, 2-aryl substituted N-acetyl tryptamine compounds (disclosed in applicant's co-pending U.S. patent applications Ser. Nos. 07/086,290 and 07/086,062, both filed Aug. 17, 1987) have been defined as melatonin receptor antagonists. The present invention relates to the use of melatonin receptor antagonist as defined by the Dubocovich assay for antidepressant agents.

Typically, melatonin has been implicated in a number of human disorders, particularly those relating to chronobiologic abnormalities. Researchers have suggested administering melatonin to alleviate or prevent disturbances in circadian rhythms caused by the rapid crossing of time zones, e.g., jet lag, or changes in work shifts from night to day. See European Patent Application 0 126 630, by Short, et al.

It has been proposed that melatonin mediates the effects of shortening days on the winter depressive symptoms of seasonal affective disorder (SAD) and that the symptoms of SAD result from secretion of melatonin, either in some abnormal way or in a population which is abnormally sensitive to its effects. See Rosenthal, et al., *J. Neural Transm.* [suppl] 21:258-267 (1986). Bright light can suppress nighttime melatonin production in humans, but ordinary indoor light does not have this effect. As stated by Lewy et al., *Psychophormecal. Bull.* 20, 561-565 (1984), these findings suggest that bright artificial light may be used to manipulate human biological rhythms. Lewy, in *Science*, Vol. 235, at pp. 352-354 (1987) uses bright light to shift the peak of nighttime melatonin production in humans and has shown that this treatment reverses the depressive symptoms of patients with SAD. Bright light has also been used to treat chronobiologic sleep disorders.

Specifically, chronobiologic sleep and mood disorders have been effectively treated with bright light which appears to shift circadian rhythms (e.g., that of melatonin). A melatonin receptor antagonist, by altering the effect of melatonin at target sites (e.g., receptors), will act in the same way as bright light. It follows that if bright light exerts an antidepressant effect or is therapeutic for sleep disorders, melatonin receptor antagonists administered instead of light will have the same therapeutic effect.

Melatonin analogues have been studied for their effects on the reproductive system, specifically antigonadal activity and inhibition of release of luteinizing hormone (LH). See Flaugh et al., *Journal of Medicinal Chemistry*, Vol. 22 at pp. 63-69.

Frohn et al., *Life Sciences*, Vol. 27, pp. 2043-2046, Pergamon Press, and Clemens et al., *J. Neural Transm.* [suppl] 21:451-459 (1986), disclose melatonin analogues wherein the activity of such analogues is related to structure. Analogues With improved metabolic stability are disclosed.

SUMMARY OF THE INVENTION

The present invention provides a new method of use for compounds defined as having melatonin antagonist activity according to the Dubocovich assay. These compounds are represented by the formula:

wherein each R is independently selected from the group consisting of hydrogen, halogen, e.g., fluoro and chloro, and lower alkyl radicals, i.e., $C_1$ to $C_4$ alkyl radicals, e.g., methyl, ethyl, n-propyl and isopropyl; $R^1$ is an aryl radical having from 4 to 14 carbon atoms, e.g., a phenyl, thienyl, furanyl, pyridyl or a naphthyl radical; $R^2$ is selected from the group consisting of hydrogen, lower alkyl, i.e., $C_1$ to $C_4$ alkyl radicals, lower alkoxy, i.e., $C_1$ to $C_4$ alkoxy and phenoxy radioals; $R^3$ is seleoted from the group consisting of hydrogen, halogen, hydroxy, lower alkyl, lower alkoxy and phenoxy radicals;

$R^4$ is selected from the group consisting of hydrogen, halogen, e.g., fluoro and chloro, hydroxy, lower alkyl, i.e., $C_1$ to $C_4$ alkyl radicals, lower alkoxy, i.e., $C_1$ to $C_4$ alkoxy and phenoxy radicals; $R^5$ is selected from the group consisting of hydrogen, halogen, e.g., fluoro and chloro, hydroxy, lower alkyl, i.e., $C_1$ to $C_4$ alkyl, lower alkoxy, i.e., $C_1$ to $C_4$ alkoxy and phenoxy; $R^6$ is selected from the group consisting of hydrogen, halogen, e.g., fluoro and chloro, hydroxy, lower alkyl, i.e., $C_1$ to $C_4$ alkyl, lower alkoxy, i.e., $C_1$ to $C_4$ alkoxy and phenoxy; and A is O, S or N; m is an integer of from 1 to 3; and x is 0 or 1, and y is 1 when A is O or S, and y is 2 when A is N.

Preferably, each R is a hydrogen radical, $R^2$ is a lower alkyl radical, m is n is 2 and x is 0. More preferably, $R^1$ is selected from the group consisting of hydrocarbyl radicals such as phenyl and naphthyl, e.g., phenyl.

In accordance with the present invention, the method described herein and the method of administration of the melatonin receptor antagonist clearly differentiates the actions of conventional antidepressants and the melatonin receptor antagonists which can be used for chronobiologic disorders by blocking the action of melatonin to provide an antidepressant effect, in disorders in which a disturbance of melatonin levels and/or rhythmicity exists.

DETAILED DESCRIPTION OF THE INVENTION $R^1$ may be selected from the group consisting of thienty, furanyl, pyridyl, pyrrolyl, and other aromatic and heteroaromatic radicals comprising single rings of five or six members; such compounds are described in co-pending U.S. patent applications Ser. Nos. 07/086,290, and 07/086,062, both filed Aug. 17, 1987.

$R^1$ may also represent polyphenyl radicals such as biphenyl and similar polyaromatic and polyheteroaromatic radicals.

$R^1$ may also be selected from the group consisting of organic radicals having fused aromatic rings; that is, radicals comprising at least two rings that share a pair of carbon atoms or a carbon and nitrogen atom. Preferably, $R^1$ comprises no more than 3 fused aromatic rings, and more preferably, $R^1$ comprises 2 fused aromatic rings. Examples of radicals suitable for $R^1$ include naphthyl, anthracyl, phenanthryl, benzofuranyl, benzothienyl, indolyl, indazolyl, benzotriazolyl, triazolophridinyl, benzoxazolyl, benzothiazolyl, benzoxadiazolyl, benzopyranyl, quinolyl, phthalazinyl, purinyl, naphthothienyl, indolizinyl, quinlizinyl, naphthyridinyl, quinoxalinyl, quinazolinyl, cinnolinyl, etc. The above radicals may also be substituted with various functional groups. In particular, such substituents may be selected from the group consisting of hydroxy, nitro, azido, sulfoanamido, halogen, and hydrocarbyl.

The above compounds may be made as described in the examples below.

Specific preferred compounds which are within the scope of this invention include:
2-benzyl-N-acetyl tryptamine
2-benzyl-5-bromo-N-acetyl tryptamine
2-benzyl-5-hydroxy-N-acetyl tryptamine
2-benzyl-5-methoxy-N-acetyl tryptamine
2-(2-chlorobenzyl)-N-acetyl tryptamine
2-(2-methylbenzyl)-N-acetyl tryptamine
2-(2-nitrobenzyl)-N-acetyl tryptamine
2-(naphthylmethyl)-N-acetyl tryptamine
2-(2-thienylmethyl)-N-acetyl tryptamine The preferred embodiment of the present invention comprises a method of treating individuals with psychiatric disorders related to altered melatonin function or influenced by melatonin and circadian rhythms, e.g., depression, by administering a therapeutically-effective amount of one or more of the compounds of the present invention to a patient suffering from one of the psychiatric disorders, namely, depression. The compound is administered in a manner to produce the same therapeutic effect of light. Conditions involving delays and advances of the sleep-wake cycle and that respond to light therapy [e.g., seasonal depression] should be amenable to treatment with melatonin receptor antagonists described in the present invention or by combination of more than one compound of the present invention.

Generally, a pharmacologically effective daily dose can be from 0.01 mg/kg to 100 mg/kg per day, and preferably from 0.1 mg/kg to 25 mg/kg per day, bearing in mind, of course, that in selecting the appropriate dosage in any specific case, consideration must be given to the patient's weight, general health, metabolism, age and other factors which influence response to the drug, and in particular, the time of administration. A particularly preferred dose is 1.0 mg/kg per day.

The pharmaceutical composition may be in a form suitable for oral use; for example, as tablets, aqueous or oil suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from the group consisting of sweetening agents, flavoring agents, coloring agents, and preserving agents in order to provide a pharmaceutically elegant and palatable preparation. Tablets contain the active ingredient in a mixture with nontoxic pharmaceutically acceptable excipients which are suitable for the manufacture of tablets. For example, these excipients may be inert diluents such as calcium carbonate, sodium carbonate, lactose, calcium phosphate, or sodium phosphate; granulating and disintegrating agents such as maize starch or alginic acid; binding agents such as starch, gelatine, or acacia; and lubricating agents such as magnesium stearate, stearic acids, or talc. The tablets may be uncoated, or they may be coated by known techniques to delay disintegration and absorption into the gastrointestinal tract, thereby providing a sustained action over a longer period.

Formulations for oral use may also be presented as hard gelatine capsules wherein the active ingredient is mixed with an inert solid diluent—for example, calcium carbonate, calcium phosphate, or kaolin—or as soft gelatine capsules wherein the active ingredient is mixed with an oil medium—for example, arachis oil, liquid paraffin, or olive oil.

Aqueous suspensions contain the active compound in admixture with excipients suitable for the manufacture of aqueous suspensions. Such excipients are suspending agents such as sodium carboxymethylcellulose, methylcellulose, hydroxypropylmethylcellulose, sodium alginate, polyvinylpyrrolidone, gum tragacanth, and gum acacia; dispersing or wetting agents may be a naturally-occurring phosphatide such as lecithin or condensation products of an alkylene oxide with long chain aliphatic alcohols (for example, heptadecaethyleneoxy-cetanol) or condensation products of ethylene oxide with partial esters derived from fatty acids and a hexitol such as polyoxyethylene sorbitol monooleate, or condensation product of ethylene oxide with partial esters derived from fatty acids and hexitol anhydrides (for example, polyoxyethylene sorbitan monooleate). The said aqueous suspensions may also contain one or more preservatives (for example, ethyl, n-propyl, or p-hydroxy benzoate), one or more coloring agents, one or more flavoring agents, and one or more sweetening agents such as sucrose, saccharin, or sodium or calcium cyclamate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients—for example, sweetening, flavoring, and coloring agents—may also be present.

Syrups and elixirs may be formulated with sweetening agents; for example, glycerol, sorbitol or sucrose. Such formulations may also contain a demulcent, a preservative, and flavoring and coloring agents. The pharmaceutical compositions may be in the form of a sterile injectable preparation; for example, as a sterile injectable aqueous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent; for example, as a solution in 1,3-butane diol.

The pharmaceutical compositions of the present invention also include compositions for transdermal and/or intranasal administration. Thus, the compounds of the present invention may be compounded with a penetration-enhancing agent such as 1-n-dodecylazacyclopentan-2-one or the other penetration-enhancing agents disclosed in U.S. Patent Nos. 3,991,203 and 4,122,170 which are hereby incorporated by reference to describe penetration-enhancing agents which may be included in the transdermal or intranasal compositions of this invention.

The pharmaceutical compositions may be tableted or otherwise formulated so that for every 100 parts by weight of the composition, there are present between 5 and 95 parts by weight of the active ingredient. The dosage unit form will generally contain between about 1 mg. and about 100 mg. of the active ingredient of the formula stated above.

From the foregoing formulation discussion, it is apparent that the compositions of this invention can be administered orally or parenterally. The term "parenterally" or "parenteral" as used herein includes subcutaneous injection; intravenous, intramuscular, or intrasternal injection or fusion techniques.

To illustrate the manner in which the invention may be carried out, the following examples are given. It is understood, however, that the examples are for the purpose of illustration, and the invention is not to be regarded as limited to any of the specific materials or conditions therein.

EXAMPLE A

Preparation of 2-benzyl-N-acetyl tryotamine (N-0774, Luzindole).

8.0 gm (0.05M) tryptamine, 5.8 gm (0.055M) benzaldehyde and 440 ml 0.125N sulfuric acid were mixed together and heated in a stirred one-liter, round-bottomed flask to 70°-75° C. for 24 hours. The resultant precipitate was filtered off and recrystallized from a solution of ethanol made basic with ammonium hydroxide. The resultant free amine had a melting point of 168°-174° C.

4.10 gm (0.026m) of the above product (1-benzyl-tetrahydrocarboline hydrochloride) was combined with 600 mg 10% palladium on carbon, 30 ml glacial acetic acid and 180 ml deionized water. This mixture was placed in a bomb under approximately 100 lbs/in$^2$ hydrogen heated to 35° C. The reaction was continued for 6 hours and then let cool to room temperature overnight. This mixture was filtered and the filtrate extracted with dichloromethane. The aqueous solution was then treated with ammonium hydroxide, and the resultant precipitate filtered off, washed with water and dried. The melting point was 159°-163° C. Yield: 2.2 gm (54%).

0.3 gm (0.0012M) of the above product (2-benzyl tryptamine) was dissolved in ethyl acetate and made basic with several drops of ammonium hydroxide. 50 mg potassium carbonate was added, with 0.3 ml (0.01M) acetic anhydride.

This mixture was stirred for 15 minutes at room temperature under nitrogen. Water was added and the organic phase separated. This was washed with brine and dried with magnesium sulfate. Concentration gave a residue which was purified by column chromatography (C-18 column, methanol/water gradient) to give 0.075 gm (21%) of 2-benzyl-n-acetyl tryptamine. Elemental analysis: C 77.94%, H 6.89%, N 9.39%. Theoretical: C 78.05%, H 6.89%, N 9.58%.

EXAMPLE 1

Melatonin Receptor Assay

Melatonin has been shown to inhibit dopamine release from rabbit retina via a specific receptor mechanism [Dubocovich, Nature, 306:782–784 (1983) and J. Pharmacol. Exp. Ther., 234:395–401 (1985)]. Competitive melatonin receptor antagonists are expected to prevent the decrease in dopamine release by melatonin and shift the melatonin concentration-response curve to higher concentrations.

Figure 1:
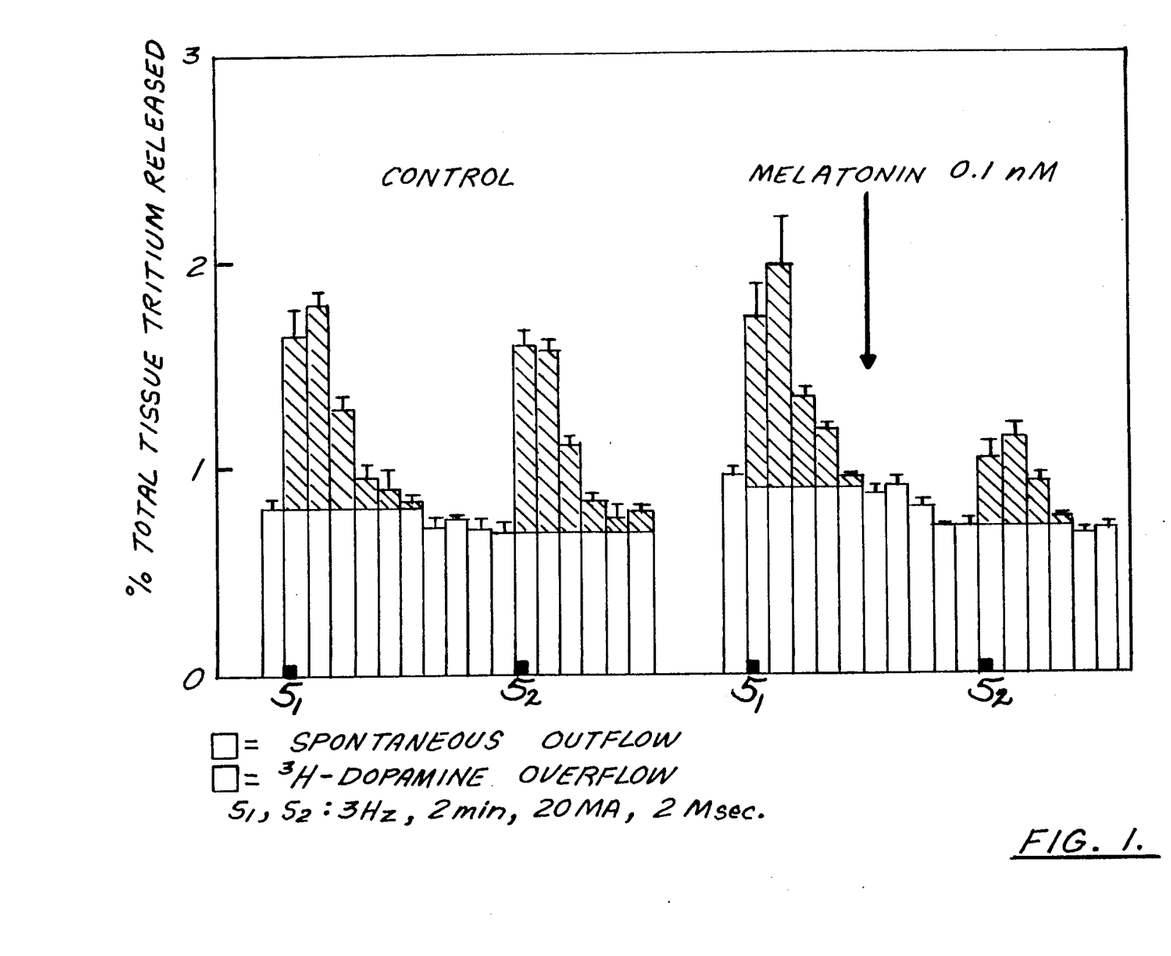
FIG. 1. is a bar graph showing the efflux of radioactivity from rabbit retina labeled with $^3$H-DA.

Method: The method of Dubocovich, 1985, was used to demonstrate melatonin receptor antagonist activity. Briefly, dopamine release was elicited in vitro by electrical field stimulation (3 Hz, 1 min. 20 mA, 2 sec.) of rabbit retinal pieces which had been prelabeled with $^3$H-dopamine. Release was determined as the percentage of total tissue radioactivity that was released during stimulation(s) minus the spontaneous release level determined before and after stimulation. Two periods of stimulation ($S_1$ and $S_2$) were applied 40 minutes apart in each experiment. Results are expressed as the ratio of release in $S_2$ to release in $S_1$ (FIG. 1.).

Drugs are added 20 minutes before the second stimulation to test their effect on the spontaneous and stimulation-evoked release of $^3$H-dopamine. Melatonin added before the second stimulation inhibits the release of $^3$H-dopamine (FIG. 1.).

This assay was used to search for melatonin antagonistic activity. First, the compounds (antagonists) were tested alone to determine their effect on spontaneous and stimulated release of dopamine (FIG. 2a.).

Figure 3A:
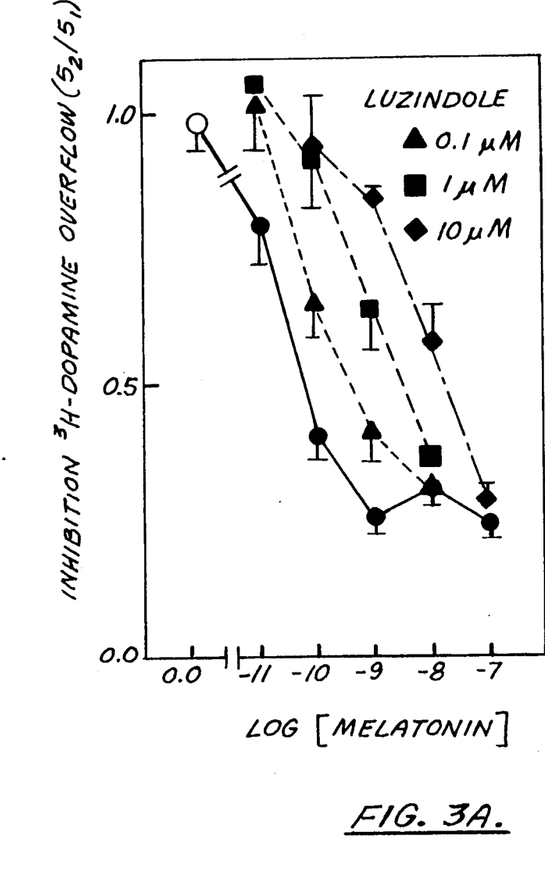
FIGS. 3a. and 3b. are bar graphs showing Luzindole (N-0774) antagonization of melatonin-induced inhibition of the calcium-dependent release of $^3$H-dopamine from rabbit retina.
Figure 3B:
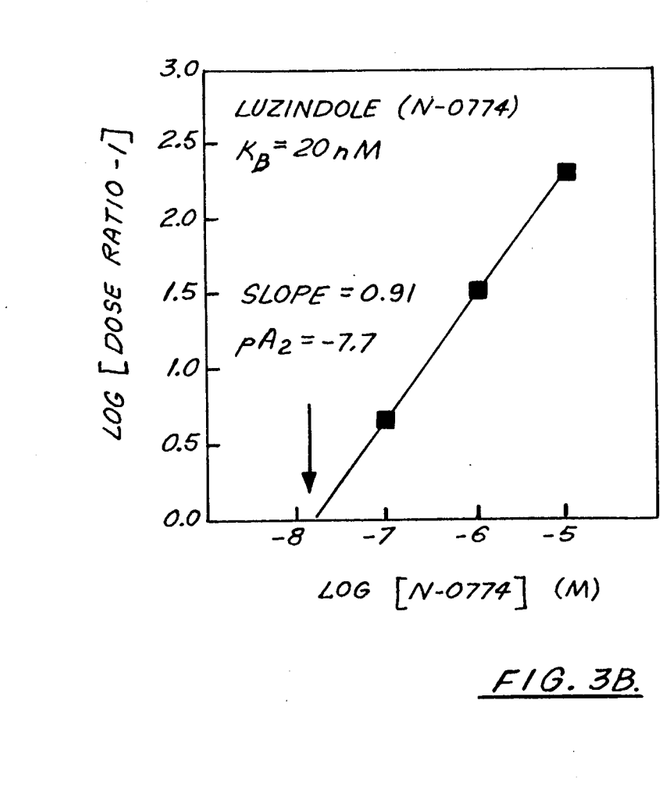

In the control experiments, melatonin at various concentrations was present during $S_2$ and release was depressed relative to that seen in $S_2$ (FIGS. 3a. and 3b.). To test for antagonist activity, a compound was added 40 minutes prior to $S_1$ and was present throughout the remainder of the experiment which involved adding melatonin during the $S_2$ period.

Figure 2A:
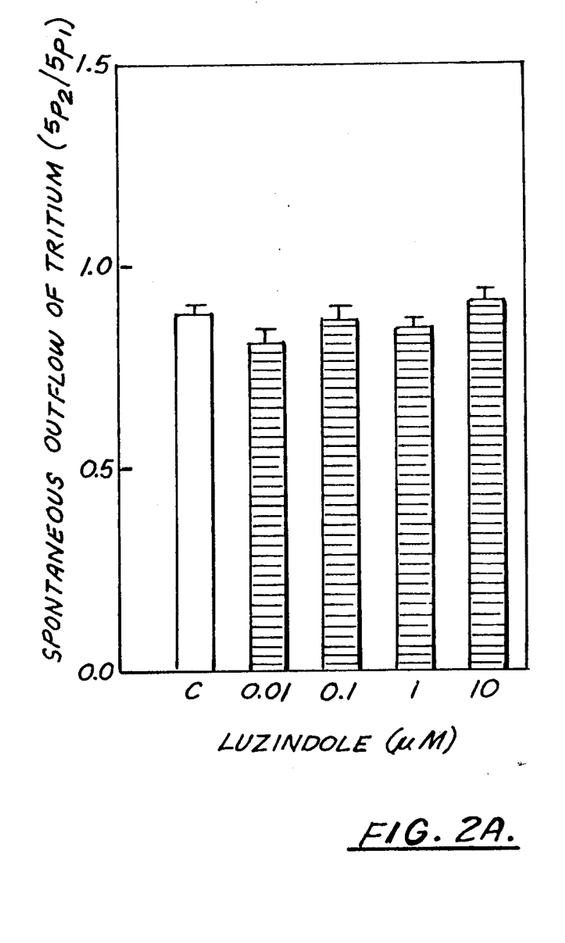
FIG. 2a. is a bar graph of spontaneous basal release for rabbit retina.
Figure 2B:
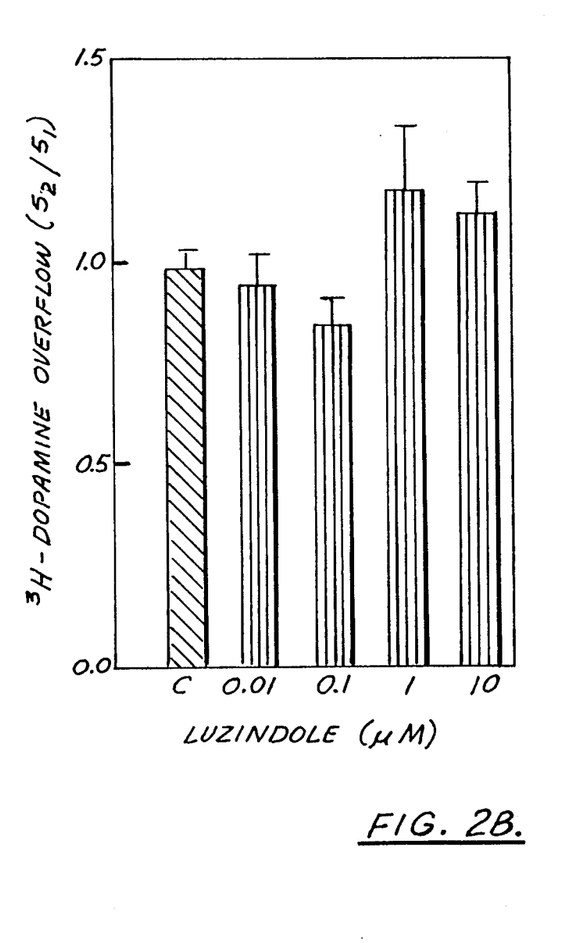
FIG. 2b. is a bar graph of calcium-dependent release of $^3$H-DA for rabbit retina.

The compound of Example A had little or no direct effects on either spontaneous or stimulated dopamine release which tested at concentrations of 0.1–10 μM (FIGS. 2a. and 2b.). As shown in FIGS. 2a. and 2b., the compound by itself did not modify the control ratio $S_{P2}/S_{P1}$ or $S_2/S_1$ The presence of increasing concentrations of melatonin in $S_2$ did progressively decrease the $S_2/S_1$ ratio (FIGS. 3a. and 3b) (0.1–10 μM). The concentration of melatonin which inhibited release by 50% ($IC_{50}$) was 0.14 μM. As shown in the figure, the effectiveness of any given melatonin concentration was decreased by increasing concentrations of this compound, and the melatonin concentration-response curves were shifted in parallel to the right (increasing the $IC_{50}$ values) (FIG. 3a.). The affinity constant ($K_B$) for antagonists can be estimated from the Schild plot [Arunlakshana and Schild, Br. J. Pharmacol., 14:48–58 1959)]; and in the case of this compound, the estimated $K_B$ was found to be 20 μM.

In FIG. 3a., the melatonin was either absent (open symbols) or present at various concentrations (filled symbols) during $S_2$ The compound of Example A was present during both $S_1$ and $S_2$ at a concentration of 0.1 μM (▲), 1 μM (■), or 10 μM (♦). Control is O.

Conclusion: The compound of Example A, 1,2-benzyl-N-acetyl tryptamine, is a potent, competitive antagonist at melatonin receptors.

EXAMPLE 2

Behavioral Despair Test for Antidepressants

Methods: Typical and atypical antidepressants reduce the time during which mice are immobile in a forced swimming test. [Porsolt et al., Arch. Int. Pharmacodun. Ther. 229:327–336 (1977)] This test, known as the behavioral despair test, appears to be a good predictor of clinical antidepressant activity.

Male albino Swiss ND/4 mice and C3H/HeN mice (4 to 5 weeks old) were purchased from Harlam Sprague Dawley (Indianapolis, Ind.). Mice of the $C^3H$/HeN strain are known to produce melatonin [Hotz, M. M., Behavioural Genetic, 15:595 (1985)]. The animals were kept in the same facilities at least two weeks before the experiment to allow them to adapt to a 14/10 hour light/dark cycle (lights on at 4 a.m./off at 6 p.m.).

Mice were housed in groups of 10 in polycarbonate plastic cages $13\frac{7}{8} \times 8\frac{5}{8} \times 5\frac{1}{8}$ inches with 88 square inches of floor space) with free access to feed (Agway 3000 rat, mouse and hamster feed) and water. During the light period, light intensity at the level of the cages was about 250 lux. The room temperature was kept constant at 22 ±1° C. The present series of experiments were conducted between October, 1986 and January, 1987.

The day of the experiment, mice were weighed, marked on the tail and placed in cages (8 mice per cage) as described above. Animals were transferred to the laboratory where the swim test was to be conducted at 10:00 a.m. for noon experiments and at 5:00 p.m. for evening experiments. For noon experiments, the swim test was started at 12:00 h and for midnight experiments, the swim test was started at 24:00 h. Two mice obtained, from different experimental groups were tested simultaneously.

Apparatus: The apparatus consisted of two glass beakers (height: 13 cm; diameter: 11.5 cm), each placed inside a bigger glass beaker (height: 20 cm; diameter: 12.4 cm) containing 6 cm of water at 23 ±1° C. A non-transparent panel placed between the two cylinders prevented the mice from seeing each other. At midnight, experiments were conducted under red dim light (Kodak, filter A) provided by two photographic safety lights located at each side of the beakers.

Drugs: Mice were injected with vehicle or drugs dissolved in vehicle dissolved at the appropriate concentrations. Each mouse received 0.1 ml of liquid/10 g body weight. Drugs were dissolved immediately before the experiment. Desipramine was obtained from Sigma (St. Louis, Mo.) and dissolved in water. Melatonin (Sigma) and N-0774 (Nelson Research, Irvine, Calif.) were suspended in 1% Tween 80 using a Plytron. Bright light was administered with a fluorescent lamp placed one foot above the mice.

Methods: The swim test was conducted as described by Porsolt et al [Arch. Int. Pharmacodyn. 229:327–336 (1977)]. Forced swim in a narrow cylinder induced a depressed state characterized by an immobile posture, which is readily identifiable. A mouse is considered to be immobile when it ceases struggling and remains floating motionless in the water, making only those movements necessary to keep its head above water. Vehicle, desipramine, melatonin or N-0774 were administered 30 minutes, 60 minutes or 120 minutes before the mice were dropped into the cylinders. Two mice that had received different treatments were observed simultaneously. Mice were dropped into the cylinders and left in the water for 6 minutes. The time of immobility was recorded during the last 4 minutes of swimming.

Results

1. In the albino Swiss ND/4 mice tested in the behavioral despair test, the time of immobility was identical in experiments conducted at noon or at midnight. These experiments suggested that the behavior of the albino Swiss ND/4 mice in this test is not affected by diurnal changes in photoperiod (Table 1).

In the albino Swiss mice, the typical antidepressant desipramine induced the same decrease in time of immobility in the behavioral despair test at noon and at midnight. In the albino Swiss mice, neither melatonin nor the melatonin receptor antagonist N-0074 modified the time of immobility in experiments conducted at noon or at midnight (Table 1).

TABLE 1

| | Albino Swiss ND/4 Mice Duration of Immobility (Sec) | |
|---|---|---|
| Drug | Noon | Midnight |
| Control | 72.4 ± 4.9 | 84.3 ± 11.2 |
| Desipramine (30 mg/kg) | 38.2 ± 5.1 | 46.0 ± 1.3 |

TABLE 1-continued

| | Albino Swiss ND/4 Mice Duration of Immobility (Sec) | |
|---|---|---|
| Drug | Noon | Midnight |
| N-0774 (30 mg/kg) | 57.4 ± 8.9 | 81.4 ± 3.9 |

2. In the C3H/HeN mice the time of immobility in the behavioral despair test was longer in experiments conducted at midnight than at noon. These experiments suggested that the behavior of these mice in the despair test is affected by diurnal changes in photoperiod (Table 2).

In the C3H/HeN mice the typical antidepressant desipramine appears to be more potent to reduce the time of immobility at midnight than at noon, perhaps suggesting a partial involvement of melatonin in the mechanism of action of this antidepressant. The melatonin receptor antagonist N-0774 reduces the time of immobility in a dose-dependent fashion, the effect being more pronounced at midnight than at noon. These experiments suggested that N-0774 exerts an antidepressant effect, possibly blocking a receptor endogenously activated by melatonin. In this test exogenous melatonin administered either at midnight or at noon did not change the time of immobility (Table 2).

TABLE 2

| | C3H/HeN Mice Duration of Immobility (Sec) | |
|---|---|---|
| Drug | Noon | Midnight |
| Control | 47.7 ± 3.4 | 67.7 ± 2.15 |
| Desipramine | | |
| (.03 mg/kg) | 46.2 ± 12.9 | 33.2 ± 7.3 |
| (3.00 mg/kg) | 20.7 ± 3.7 | 16.1 ± 6.0 |
| (10.00 mg/kg) | 20.7 ± 2.0 | 13.2 ± 7.2 |
| N-0774 | | |
| (.03 mg/kg) | 53.8 ± 8.8 | 47.7 ± 4.7 |
| (3.00 mg/kg) | 37.4 ± 6.6 | 16.1 ± 5.2 |
| (10.00 mg/kg) | 52.1 ± 6.8 | 13.1 ± 3.6 |
| Melatonin | | |
| (30.00 mg/kg) | 45.9 ± 18.0 | 57.9 ± 9.0 |

3. In experiments conducted at noon (when the endogenous levels of melatonin are low), in-darkness administration of melatonin increased the time of immobility in the C3H/HeN mice suggesting that endogenous melatonin may play a role in the performance of the behavioral despair test (Table 3). Moreover, we found that the time of immobility at midnight in C3H/HeN mice, which had been kept one week in constant light in order to inhibit the synthesis of melatonin by the pineal gland, the time of immobility in the behavioral despair test was identical to that found at noon. These experiments further suggest that the antidepressant effect of melatonin receptor antagonists may depend on the presence of endogenous melatonin.

TABLE 3

| | C3H/HeN Mice Duration of Immobility (Sec) |
|---|---|
| Drug | Noon (In-Darkness Administration) |
| Control | 29.5 ± 3.34 |
| Melatonin (30 mg/kg) | 48.2 ± 5.02 |

4. It has also been found that exposure to bright light (more than 2,500 lux) at midnight decreases the time of immobility, as observed with N-0774. These experiments suggest that melatonin receptor antagonists should have the same antidepressant effects as light (Table 4).

TABLE 4

| | Duration of Immobility (Sec) |
|---|---|
| Drug | Midnight |
| Control | 67.7 ± 2.15 |
| N-0774 (10 mg/kg) | 16.1 ± 5.20 |
| Bright Light | 31.0 ± 10.00 |

What is claimed is:

1. A method for reducing depression in a human which comprises administering to said human an antidepressive amount of at least one of the compounds represented by the following formula:

wherein each R is independently selected from the group consisting of hydrogen, halogen, e.g, fluoro and chloro, and lower alkyl, i.e., $C_1$ to $C_4$ alkyl, e.g., methyl, ethyl, n-propyl and isopropyl; $R^1$ is a hydrocarbyl aryl having from 4 to 14 carbon atoms; $R^2$ is selected from the group consisting of hydrogen, lower alkyl, i.e., $C_1$ to $C_4$ alkyl, lower alkoxy, i.e., $C_1$ to $C_4$ alkoxy and phenoxy; $R^3$ is selected from the group consisting of hydrogen, halogen, hydroxy, lower alkyl, lower alkoxy and phenoxy; $R^4$ is selected from the group consisting of hydrogen, halogen, e.g., fluoro and chloro, hydroxy, lower alkyl, i.e., $C_1$ to $C_4$ alkoxy and phenoxy; $R^5$ is selected from the group consisting of hydrogen, halogen, e.g., fluoro and chloro, hydroxy, lower alkyl, i.e., $C_1$ to $C_4$ alkyl, lower alkoxy, i.e., $C_1$ to $C_4$ alkoxy and phenoxy; $R^6$ is selected from the group consisting of hydrogen, halogen, e.g., fluoro and chloro, hydroxy, lower alkyl, i.e., $C_1$ to $C_4$ alkyl, lower alkoxy, i.e., $C_1$ to $C_4$ alkoxy and phenoxy; and A is O, S or N; m is an integer of from 1 to 3; n is an integer of from 1 to 3 and x is 0 or 1, and y is 1 when A is O or S, and y is 2 when A is N.

2. A method for reducing depression in a mammal which comprises administering to said human antidepressive amount of one or more compounds represented by the following formula:

wherein each R is independently selected from the group consisting of hydrogen halogen and $C_1$ to $C_4$ alkyl radicals; $R^1$ is a hydrocarbyl aryl radical; $R^2$ is selected from the group consisting of hydrogen, $C_1$ to $C_4$ alkyl, $C_1$ to $C_4$ alkoxy and phenoxy radicals;

$R^3$ is selected from the group consisting of hydrogen, halogen hydroxy, lower alkyl, lower alkoxy and phenoxy radicals; $R^4$ is selected from the group consisting of hydrogen, halogen, hydroxy, lower alkyl, $C_1$ to $C_4$ alkoxy and phenoxy radicals; $R^5$ is selected from the group consisting of hydrogen, halogen, hydroxy, $C_1$ to $C_4$ alkyl, $C_1$ to $C_4$ alkoxy and phenoxy radicals;

$R^6$ is selected from the group consisting of hydrogen, halogen, hydroxy, $C_1$ to $C_4$ alkyl, $C_1$ to $C_4$ alkoxy and phenoxy radicals;

A is O, S or N; m is an integer of from 1 to 3; n is an integer of from 1 to 3 and X is 0 or 1 and y is 1 when X is O or A is O or S, and y is 2 when A is N.

3. The method of claim 2 wherein in the compound, each R is a hydrogen, $R^2$ is a lower alkyl, M is 1, N is 2, and X is 0.

4. The method of claim 2 wherein R3, $R^4$, $R^5$ and $R^6$ of the compound are hydrogen.

5. The method of claim 2 wherein $R^1$ is selected from the group consisting of phenyl, naphthyl, p-methyl phenyl and p-methoxy phenyl.

6. The method of claim 2 wherein $R^3$ is a methoxy and $R^4$, $R^5$ and $R^6$ are hydrogen.

7. The method of claim 2 wherein $R^1$ is a phenyl.

8. The method of claim 2 wherein $R^1$ is a naphthyl.

9. The method of claim 2 wherein $R^1$ is a p-methyl phenyl.

10. The method of claim 2 wherein $R^1$ is a p-methoxy phenyl radical.

11. The method of claim 2 wherein the anitdepressive amount of the compound is from about 0.01 to about 100 mg/kg per day.

12. The method of claim 2 wherein the antidepressive amount of the compound is from about 0.1 to about 25 mg/kg per day.

13. The method of claim 2 wherein the mammal is a human;

14. A method for blocking physiological effects of melatonin in mammals comprising administering to a mammal an effective amount of a compound represented by the formula:

wherein each R is independently selected from the group consisting of hydrogen, halogen and $C_1$ to $C_4$ alkyl radicals; $R^1$ is a hydrocarbyl aryl radical; $R^2$ is selected from the group consisting of hydrogen, $C_1$ to $C_4$ alkyl, $C_1$ to $C_4$ alkoxy and phenoxy radicals;

$R^3$ is selected from the group consisting of hydrogen, halogen, hydroxy, lower alkyl, lower alkoxy and phenoxy radicals; $R^4$ is selected from the group consisting of hydrogen, halogen, hydroxy, lower alkyl, $C_1$ to $C_4$ alkoxy and phenoxy radicals; $R^5$ is selected from the group consisting of hydrogen, halogen, hydroxy, $C_1$ to $C_4$ alkyl, $C_1$ to $C_4$ alkoxy and phenoxy radicals;

$R^6$ is selected from the group consisting of hydrogen, halogen, $C_1$ to $C_4$ alkyl, $C_1$ to $C_4$ alkoxy and phenoxy radicals;

A is O, S or N; m is an integer of from 1 to 3; n is an integer of from 1 to 3 and X is 0 or 1 and y is 1 when X is O or A is O or S, and y is 2 when A is N.

15. The method of claim 14 wherein said mammal is a human.

16. The method of claim 2 wherein X is O.

17. A method for reducing depression in mammals, including humans, which comprises administering to a mammal an effective amount of a compound represented by the formula:

wherein each R is independently selected from the group consisting of hydrogen, halogen, e.g., fluoro and chloro, and lower alkyl, i.e., $C_1$ to $C_4$ alkyl, e.g., methyl, ethyl, n-propyl and isopropyl; $R^1$ is a hydrocarbyl aryl having from 4 to 14 carbon atoms; $R^2$ is selected from the group consisting of hydrogen, lower alkyl, i.e., $C_1$ to $C_4$ alkyl, lower alkoxy, i.e., $c_1$ to $C_4$ alkoxy and phenoxy; $R^3$ is selected from the group consisting of hydrogen, halogen, hydroxy, lower alkyl, lower alkoxy and phenoxy; $R^4$ is selected from the group consisting of hydrogen, halogen, e.g., fluoro and chloro, hydroxy, lower alkyl, i.e., $C_1$ to $C_4$ alkyl, lower alkoxy, i.e., $C_1$ to $C_4$ alkoxy and phenoxy; $R^5$ is selected from the group consisting of hydrogen, halogen, e.g., fluoro and chloro, hydroxy, lower alkyl, i.e., $C_1$ to $C_4$ alkyl, lower alkoxy, i.e., $C_1$ to $C_4$ alkoxy and phenoxy; $R^6$ is selected from the group consisting of hydrogen, halogen, e.g., fluoro and chloro, hydroxy, lower alkyl, i.e., $C_1$ to $C_4$ alkyl, lower alkoxy, i.e., $C_1$ to $C_4$ alkoxy and phenoxy; and A is O, S or N; m is an integer of from 1 to 3; n is an integer of from 1 to 3 and x is 0 or 1, and y is 1 when A is O or S, and y is b 2 when A is N, wherein said compound is administered in a manner to coincide with the treatment of light therapy.

18. A method for blocking physiological effects of melatonin in mammals, including humans, comprising administering to a mammal an effective amount of a compound represented by the formula:

wherein each R is independently selected from the group consisting of hydrogen, halogen, e.g., fluoro and chloro, and lower alkyl, i.e., $C_1$ to $C_4$ alkyl, e.g., methyl, ethyl, n-propyl and isopropyl; $R^1$ is a hydrocarbyl aryl $R^2$ is selected from the group consisting of hydrogen, lower alkyl, i.e., $C_1$ to $C_4$ alkyl, lower alkoxy, i.e., $C_1$ to $C_4$ alkoxy and phenoxy; $R^3$ is selected from the group consisting of hydrogen, halogen, hydroxy, lower alkyl, lower alkoxy and phenoxy; $R^4$ is selected from the group consisting of hydrogen, halogen, e.g., fluoro and chloro, hydroxy, lower alkyl, i.e., $C_1$ to $C_4$ alkyl lower alkoxy, i.e., $C_1$ to $C_4$ alkoxy and phenoxy; $R^5$ is selected from the group consisting of hydrogen halogen, e.g., fluoro and chloro, hydroxy, lower alkyl, i.e., $C_1$ to $C_4$ alkyl, lower alkoxy, i.e., $C_1$ to $C_4$ alkoxy and phenoxy; $R^6$ is selected from the group consisting of hydrogen, halogen, e.g., fluoro and chloro, hydroxy, lower alkyl, i.e., $C_1$ to $C_4$ alkyl, lower alkoxy, i.e., $C_1$ to $C_4$ alkoxy and phenoxy; and A is O, S or N; m is an integer of from 1 to 3; n is an integer of from 1 to 3; and x is 0 or 1, and y is 1 when A is O or S, and y is b 2 when A is N, wherein said compound is administered in a manner to coincide with the treatment of light therapy.

* * * * *